(12) United States Patent
Liang et al.

(10) Patent No.: US 9,808,536 B2
(45) Date of Patent: Nov. 7, 2017

(54) **HYPERICIN ALBUMIN NANOPARTICLE-*ESCHERICHIA COLI* SERUM ANTIBODY COMPLEX AND PREPERATION METHOD AND APPLICATION THEREOF**

(71) Applicant: LANZHOU INSTITUTE OF HUSBANDRY AND PHARMACEUTICAL SCIENCES OF CAAS, Lanzhou, Gansu Province (CN)

(72) Inventors: Jianping Liang, Lanzhou (CN); Wenzhu Guo, Lanzhou (CN); Baocheng Hao, Lanzhou (CN); Lei Tao, Lanzhou (CN); Yu Liu, Lanzhou (CN); Xuehong Wang, Lanzhou (CN); Ruofeng Shang, Lanzhou (CN); Zhiting Guo, Lanzhou (CN); Fengwu Zhao, Lanzhou (CN); Zhen Yang, Lanzhou (CN); Hong Chen, Lanzhou (CN); Zhong Jia, Lanzhou (CN)

(73) Assignee: LANZHOU INSTITUTE OF HUSBANDRY AND PHARMACEUTICAL SCIENCES OF CAAS, Lanzhou (CN)

(*) Notice: Subject to any disclaimer, the term of this patent is extended or adjusted under 35 U.S.C. 154(b) by 0 days.

(21) Appl. No.: 15/081,657

(22) Filed: Mar. 25, 2016

(65) Prior Publication Data
US 2016/0324978 A1 Nov. 10, 2016

(30) Foreign Application Priority Data

May 5, 2015 (CN) .......................... 2015 1 0223043

(51) Int. Cl.
| | |
|---|---|
| A61K 39/00 | (2006.01) |
| A61K 39/38 | (2006.01) |
| A61K 39/108 | (2006.01) |
| A61K 47/48 | (2006.01) |
| C07K 16/12 | (2006.01) |
| C07K 14/76 | (2006.01) |

(52) U.S. Cl.
CPC .. *A61K 47/48507* (2013.01); *A61K 47/48884* (2013.01); *C07K 14/76* (2013.01); *C07K 16/1232* (2013.01); *A61K 2039/505* (2013.01)

(58) Field of Classification Search
CPC .... A61K 39/00; A61K 39/0002; A61K 39/02; A61K 39/0258
USPC ... 424/93.1, 93.4, 93.5, 184.1, 234.1, 241.1, 424/274.1
See application file for complete search history.

*Primary Examiner* — Rodney P Swartz
(74) *Attorney, Agent, or Firm* — Jiwen Chen

(57) ABSTRACT

The present invention discloses a hypericin albumin nanoparticle-*Escherichia coli* serum antibody complex, which is obtained through adding mixed hypericin albumin nanoparticles and rabbit anti-*Escherichia colis* into ethanediol, irradiating them with carbon ion, setting them at a low temperature for 2 hours after irradiation, centrifuging them at a low temperature, and freezing and drying the precipitates. Its preparation method and application are also provided. The beneficial effects of the present invention are as follows: the present invention provides a hypericin albumin nanoparticle-*Escherichia coli* serum antibody complex and its preparation method and application, wherein through bacteriostatic test and clinical pharmacodynamic test, it is proved that the effects of target complex is greatly improved compared with that of the prior drug, because the *Escherichia coli* serum antibodies seek and capture *Escherichia coli* and the hypericin albumin nanoparticles inhibit and kill *Escherichia coli*, which precisely attacks *Escherichia coli* and strengthen the antibacterial effect of hypericin albumin nanoparticle on chicken focus location.

4 Claims, 2 Drawing Sheets

HYPERICIN ALBUMIN NANOPARTICLE-*ESCHERICHIA COLI* SERUM ANTIBODY COMPLEX AND PREPERATION METHOD AND APPLICATION THEREOF

The present application claims the priority benefit of Chinese Application No. 201510223043.0, filed May 5, 2015, which is hereby incorporated by reference.

TECHNICAL FIELD

The present invention involves the field of veterinary medicinal products, specifically concerning to a hypericin albumin nanoparticle-*Escherichia coli* serum antibody complex and preparation method and application thereof.

BACKGROUND OF THE INVENTION

The research and development of polymer material has been a hot topic conducted by scholars in many countries for many years. Ion irradiation can cause changes in microstructure and macro-performance of material, so it can be used in the research on transforming polymer material. In the early phase, low ionizing radiation particles (such as Gamma ray, electron and so on) were mainly used as irradiation source. Studies found that the irradiation could generate effects in the polymer, mainly including fracture and cross-linking of molecular bond, release of gas molecule and formation of new chemical bond. The fracture and cross-linking of molecular bond could change molecular weight of material and its distribution, thus affecting the macro-performance of material. In general, the cross-linking of molecular chain could increase the molecular weight and reduce solubility and absorbance of the biomaterial. These phenomena triggered by low ionizing radiation had been fully researched and had been widely used in business application. In material, heavy ions lose energy mainly through ionizing and stimulating electrons of the target atom. Unlike low ionizing radiation particles, the heavy ions have very high electronic stopping power (linear energy transfer value LET), so heavy ions cause charge transfer and energy deposition. Consequently, when ions pass through medium, a continuous columnar ionization area can be left along its path, thus generating cross-linking and forming stable complex without causing loss of biological activity. This effect provides a method for researching complex in biological medicine.

Hypericin is a main active ingredient substance of *Hypericum perforatum* L., a guttiferae *hypericum*, and its structure belongs to naphthyl dianthrone compound. By virtue of its antiretroviral effect in vivo and in vitro and extremely strong anti-virus, antisepsis and anti-inflammation effects, hypericin can activate mononuclear phagocyte and strengthen immunity of the organism of poultry.

Lanzhou Institute of Husbandry and Pharmaceutical Sciences of CAAS had conducted extraction, chemical synthesis and veterinary clinical application related to hypericin, thus making the application of hypericin products in veterinary diseases more widely. Through clinical trials in vivo and in vitro, the curative ratio for yellow scour and white scour of newborn pigs and *pullorum* disease caused by *Escherichia coli* is over 95%. Targeting preparation, also known as targeting drug system (TDS or targeted drug delivery system, TDDS), is a new drug delivery system that could concentrate and locate drugs at lesion tissue, organ, cell or intracellular structure. Targeted therapy could significantly increase drug concentration of treated areas, decrease drug dosage, lower treatment costs, and reduce toxic side effect of drugs on the whole body. At present, targeting preparation is mainly used in cancer drugs of humans and no veterinary usage in clinic is reported. The inventors of the present invention conducted cross-linking combination of Chinese medicine ingredient hypericin with antibody and ethanediol through heavy ion irradiation to build "biological missile", thus conducting research on implementing "precise strike" to pathogenic bacteria. Results of the present invention showed that low dose of carbon ion irradiation could cause cross-linking of bio-molecules without affecting their structures and activities. The utilization of heavy ion cross-linking technology provides a new pathway for cross-linking of bio-molecules.

SUMMARY OF THE INVENTION

The object of the present invention is to provide a hypericin albumin nanoparticle-*Escherichia coli* serum antibody complex and preparation method and application thereof according to the above defects of existing technologies.

To realize the above object, the present invention provides the following technical plan: a hypericin albumin nanoparticle-*Escherichia coli* serum antibody complex is prepared through the following steps:
1) mixing the hypericin albumin nanoparticles and rabbit anti-*Escherichia coli* to obtain the mixed liquor;
2) adding the mixed liquor from Step 1) into ethanediol to obtain the ethanediol mixed liquor;
3) irradiating the ethanediol mixed liquor from Step 2) with carbon ion, placing the irradiated ethanediol mixed liquor at −2° C.-5° C. for 2 hours after irradiation to obtain the mixed liquor after irradiation;
4) centrifuging the mixed liquor after irradiation from Step 3) at a low temperature, discarding the supernatant, and freezing and drying precipitates to obtain the hypericin albumin nanoparticle-*Escherichia coli* serum antibody complex.

Further, for the above hypericin albumin nanoparticle-*Escherichia coli* serum antibody complex, hypericin albumin nanoparticles and rabbit anti-*Escherichia coli* are mixed according to (800-1600) mg:(4-10) μg in Step 1).

Further, for the above hypericin albumin nanoparticle-*Escherichia coli* serum antibody complex, the ratio of hypericin albumin nanoparticle:ethanediol is (800-1600) mg:(12-30) g in Step 2).

Further, for the above hypericin albumin nanoparticle-*Escherichia coli* serum antibody complex, the irradiation dose of carbon ion is 3-10 Gy in Step 3).

Further, for the above hypericin albumin nanoparticle-*Escherichia coli* serum antibody complex, the low temperature centrifugation is −2° C.-5° C., centrifugal rotational speed is 16500 r/min and cryogenic temperature of precipitates is −2-0° C. in Step 4).

Further, for the above hypericin albumin nanoparticle-*Escherichia coli* serum antibody complex, hypericin albumin nanoparticles and rabbit anti-*Escherichia coli* are mixed according to 1600 mg:4 μg in Step 1); the ratio of hypericin albumin nanoparticle:ethanediol is 1600 mg:12 g in Step 2); the irradiation dose of carbon ion is 5 Gy and the temperature is 0° C. in Step 3); the temperature of low temperature centrifugation is 0° C., the centrifugal rotational speed is 16500 r/min and the cryogenic temperature of precipitates is −1° C. in Step 4).

The second object of the present invention is to provide a preparation method for a hypericin albumin nanoparticle-*Escherichia coli* serum antibody complex, including the following steps:

1) mixing the hypericin albumin nanoparticles and rabbit anti-*Escherichia coli* to obtain the mixed liquor;
2) adding the mixed liquor from Step 1) into ethanediol to obtain the ethanediol mixed liquor;
3) irradiating the ethanediol mixed liquor from Step 2) with carbon ion, place the irradiated ethanediol mixed liquor at −2° C.-5° C. for 2 hours after irradiation to obtain the mixed liquor after irradiation;
4) centrifuging the mixed liquor after irradiation from Step 3) at a low temperature, discarding the supernatant, and freezing and drying precipitates to obtain the hypericin albumin nanoparticle-*Escherichia coli* serum antibody complex.

Further, the preparation method of the above hypericin albumin nanoparticle-*Escherichia coli* serum antibody complex lies in that the hypericin albumin nanoparticles and rabbit anti-*Escherichia coli* are mixed according to (800-1600) mg:(4-10) μg in Step 1); the ratio of hypericin albumin nanoparticles:ethanediol is (800-1600) mg:(12-30) g in Step 2); the irradiation dose of carbon ion is 3-10 Gy in Step 3); the temperature of low temperature centrifugation is −2° C.-5° C., the centrifugal rotational speed is 16500 r/min and the cryogenic temperature of precipitates is −2-0° C. in Step 4).

Further, the preparation method of the above hypericin albumin nanoparticle-*Escherichia coli* serum antibody complex lies in that the hypericin albumin nanoparticle and rabbit anti-*Escherichia coli* is mixed according to 1600 mg:4 μg in Step 1); the ratio of hypericin albumin nanoparticles:ethanediol is 1600 mg:12 g in Step 2); the irradiation dose of carbon ion is 5 Gy and the temperature is 0° C. in Step 3); the temperature of low temperature centrifugation is 0° C., the centrifugal rotational speed is 16500 r/min and the cryogenic temperature of precipitates is −1° C. in Step 4).

The third object of the present invention is to provide an application method of a hypericin albumin nanoparticle-*Escherichia coli* serum antibody complex in preparing *Escherichia coli* targeted drug.

Table 1 shows the screening of combination condition of rabbit antiserum and hypericin albumin nanoparticles. Hypericin albumin nanoparticles and rabbit anti-*Escherichia coli* serum are added into a prepared small centrifuge tube with micropipette according to the doses in Table 1. After adding sample, the mixture is fully shaken. Weigh appropriate amount of ethanediol on electronic balance according to Table 1. Hypericin albumin nanoparticles and rabbit anti-*Escherichia coli* serum antibodies are divided into six different dose groups with different proportions according to data in Table 1. All tubes are fully shaken. Control reaction temperature is −2° C.-5° C., irradiation cross-linking is conducted at room temperature (3-10 Gy), pH is controlled as neutral, time is set at 2 and precipitates are recovered. Results showed that the maximum yield coefficient was obtained with the concentration ratio of 1600:4:12:5 for hypericin albumin nanoparticle (mg):rabbit antiserum (μg):ethanediol (g), with yield coefficient up to 77.19% and precipitates of 10499 mg; while the maximum mass of precipitates was obtained at the concentration ratio of 1600:4:18:10, with the mass of precipitates of 11195 mg. Taking costs and drug content into consideration, the concentration ratio of 1600:4:12:5 was determined as the best ratio.

The Chinese patent application A Preparation Method for Hypericin Albumin Nanoparticles (Application No. CN201210020213.1, Publication No. CN102525937B) is hereby incorporated by reference showing the preparation of hypericin albumin nanoparticles.

TABLE 1

| Tube No. | No. 1 | No. 2 | No. 3 | No. 4 | No. 5 | No. 6 |
|---|---|---|---|---|---|---|
| Hypericin Albumin Nanoparticles (mg) | 1,000 | 1,000 | 1,600 | 1,600 | 800 | 800 |
| Rabbit Antiserum (μg) | 6 | 6 | 4 | 4 | 10 | 10 |
| Ethanediol (g) | 12 | 18 | 12 | 18 | 15 | 30 |
| Irradiation Dose of Carbon Ion (Gy) | 5 | 8 | 5 | 10 | 3 | 10 |
| Reaction Temperature (° C.) | −2 | −1 | 0 | 1 | 3 | 5 |
| Solid Weight (mg) | 6,080 | 6,200 | 10,499 | 11,195 | 5,089 | 5,249 |
| Yield Coefficient % | 46.76 | 32.26 | 77.19 | 57.11 | 32.20 | 17.04 |

The present invention is to generate polyethylene glycol from ethanediol through irradiation of carbon ion and successfully couple with hypericin albumin nanoparticle and *Escherichia coli* serum antibody, thus preparing veterinary targeted hypericin albumin nanoparticle complex specially for *Escherichia coli*. *Escherichia coli* serum antibody is responsible for seeking and capturing *Escherichia coli* and hypericin is responsible for inhibiting and killing *Escherichia coli*, making "precise attack" to *Escherichia coli*, so as to strengthen the targeted antibacterial effects of hypericin. See FIG. 1 and FIG. 2 for the structure of hypericin and antibody.

Beneficial effects of the present invention are as follows: the present invention provides a hypericin albumin nanoparticle-*Escherichia coli* serum antibody complex and preparation method and application thereof, the present invention proves that the effects of target complex are greatly increased compared with that of original drug through bacteriostatic test and clinical pharmacodynamic test. *Escherichia coli* serum antibody is responsible for seeking and capturing *Escherichia coli* and hypericin is responsible for inhibiting and killing *Escherichia coli*, making "precise attack" to *Escherichia coli*, so as to strengthen the antibacterial effects of hypericin albumin nanoparticles on chicken focus location.

DETAILED EMBODIMENTS OF THE INVENTION

Embodiment 1

Figure 1:
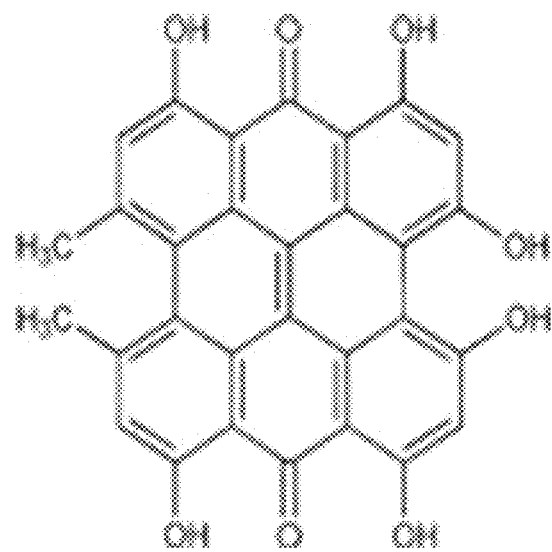
FIG. 1 is the structure diagram of hypericin.
Figure 2:
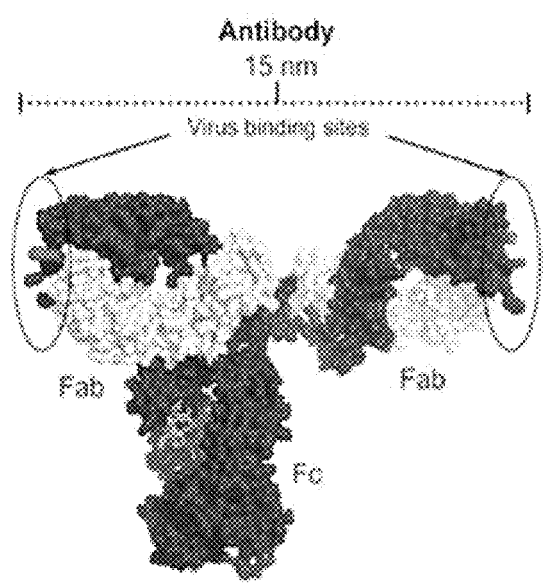
FIG. 2 is the structure diagram of antibody.
Figure 3:
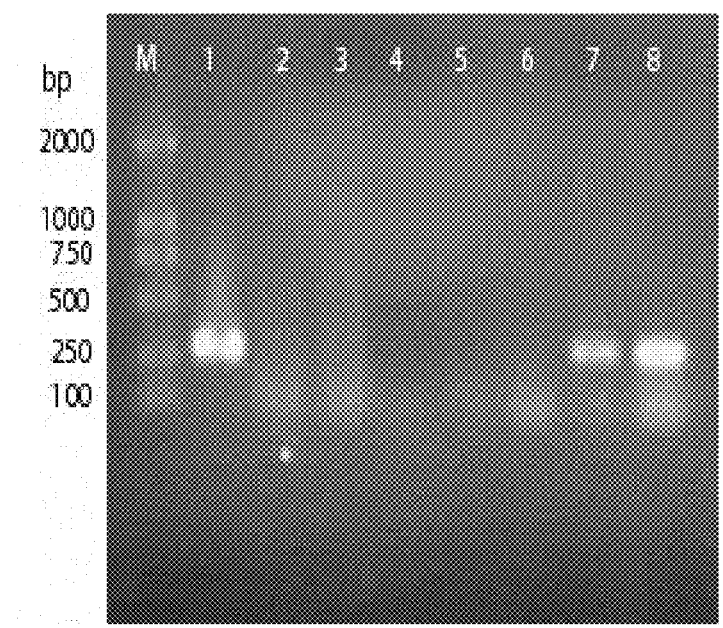
FIG. 3 is the electrophoresis result diagram of polyacrylamide gel electrophoresis (PAGE).
Among which Lane M: protein Marker; Lane 1: mixture of hypericin albumin nanoparticles and hypericin; Lane 2: hypericin albumin nanoparticles; Lane 3: mixture of hypericin albumin nanoparticles, hypericin and polyethylene glycol; Lane 4: hypericin; Lane 5: polyethylene glycol; Lane 6: rabbit antiserum; Lane 7: mixture of rabbit antiserum, drug and conjugate thereof; Lane 8: targeted conjugate.

A hypericin albumin nanoparticle-*Escherichia coli* serum antibody complex is composed by the following components: 1600 mg of hypericin albumin nanoparticles, 4 μg of rabbit antiserum and 12 g of ethanediol.

Its preparation method comprises the following steps:

hypericin albumin nanoparticles (including 1,600 mg of hypericin) were weighted according to proportion and added into 4-10 ml of *Escherichia coli* rabbit serum antibody containing 4 μg of rabbit antiserum (purchased from Shanghai Fusheng Industrial Co., Ltd.). Then 12 g of ethanediol was added, stirred at constant speed at 18-20° C. according to aseptic manipulation, and implement heavy ion irradiation. After irradiation, the irradiated ethanediol mixture was placed in a refrigerator at 40° C. for 2 hours, the irradiated ethanediol mixture was separated through refrigerated centrifuge (Hunan Xiangyi: H1650R Table-top & High-speed Refrigerated Centrifuge, 16500 r/min, −2° C.), supernatant was discarded, and the precipitates were frozen and dried to obtain hypericin albumin nanoparticle-*Escherichia coli* serum antibody complex.

Embodiment 2

Specific embodiment was the same as that of Embodiment 1 and the differences were as follows:

Hypericin albumin nanoparticle-*Escherichia coli* serum antibody complex was composed by the following components: 800 mg of hypericin albumin nanoparticles, 4 μg of rabbit antiserum and 30 g of ethanediol.

Its preparation method was the same as that of Embodiment 1.

Embodiment 3

Specific embodiment was the same as that of Embodiment 1 and the differences were as follows:

Hypericin albumin nanoparticle-*Escherichia coli* serum antibody complex was composed by the following components: 1200 mg of hypericin albumin nanoparticles, 6 μg of rabbit antiserum and 15 g of ethanediol.

Its preparation method was the same as that of Embodiment 1.

Embodiment 4

Specific embodiment was the same as that of Embodiment 1 and the differences were as follows:

Hypericin albumin nanoparticle-*Escherichia coli* serum antibody complex was composed by the following components: 1000 mg of hypericin albumin nanoparticles, 4 μg of rabbit antiserum and 18 g of ethanediol.

Its preparation method was the same as that of Embodiment 1.

Embodiment 5

Hypericin albumin nanoparticle-*Escherichia coli* serum antibody complex was prepared by carbon ion irradiation:

To build antibody targeted drug for bacteria and make antibody carrying drug that actively moves to bacteria, it is required to combine antibody with the drug to form a complex and the complex shall have certain stability. Meanwhile, the combination of antibody and drug cannot start chemical reaction or destroy biological activity of antibody and antibacterial effects of the drug to ensure the targeting effect of antibody and antibacterial effect of the drug. Therefore, it is essential to establish scientific method for the combination of antibody and drug. The present invention applied ethanediol as raw material of conjugates, implements cross-linking for *Escherichia coli* serum antibody and hypericin albumin nanoparticles through heavy ion irradiation, caused ethanediol to form polyethylene glycol and combined *Escherichia coli* serum antibody with hypericin albumin nanoparticles to form a complex.

1. Experimental Materials:

*Escherichia coli* rabbit serum antibody: purchased from Shanghai Fusheng Industrial Co., Ltd.;

Hypericin albumin nanoparticles (self-manufactured);

Hypericin: Shanghai Biochempartner Co., Ltd. (content of 98%);

Ethanediol: Tianjin Reagent No. 1 Factory (AR).

2. Heavy Ion Accelerator:

National Laboratory of Heavy Ion Accelerator in Lanzhou of Institute of Modern Physics, Chinese Academy of Sciences, provided radiation beam required by irradiation.

3. Preparation Method:

Table 2 showed the screening of combination condition of rabbit antiserum and hypericin albumin nanoparticles. The effective combination method for rabbit antiserum, ethanediol and hypericin albumin nanoparticles was selected. The conditions for the combination of antibody, ethanediol and hypericin albumin nanoparticle were screened: Micropipettes were used to add hypericin albumin nanoparticles and rabbit anti-*Escherichia coli* serum into a prepared small centrifuge tube according to the doses in Table 2. After adding sample, the mixture was thoroughly shaken. An appropriate amount of ethanediol was weighed on an electronic scale according to Table 2. Hypericin albumin nanoparticles, ethanediol and rabbit anti-*Escherichia coli* serum were divided into different proportions, and divided into six different dose groups according to data in Table 2.

TABLE 2

| Tube No. | 1 | 2 | 3 | 4 | 5 | 6 |
|---|---|---|---|---|---|---|
| Hypericin Albumin Nanoparticles (mg) | 1,000 | 1,000 | 1,600 | 1,600 | 800 | 800 |
| Rabbit Antiserum (μg) | 6 | 6 | 4 | 4 | 10 | 10 |
| Ethanediol (g) | 12 | 18 | 12 | 18 | 15 | 30 |
| Irradiation Dose (Gy) | 5 | 8 | 5 | 10 | 3 | 10 |

All tubes were fully shaken. After irradiated by heavy ion accelerator, the irradiated ethanediol mixture was placed in thermostat at 4° C. for 24 hours. Then the irradiated ethanediol mixtures were taken out to observe precipitates.

4. Detect the Combination of Antibody, Ethanediol and Hypericin Albumin Nanoparticles and its Stability:

PAGE electrophoresis: 10% separation gel and 5% spacer gel were prepared. Electrophoresis samples were antibody, complex and mixture, with 204, of sample for each lane.

5. Results and Analysis:

The present invention mainly used specific antigen-antibody immunological reaction to combine specific targeting effect of *Escherichia coli* rabbit antiserum with the bactericidal effect of hypericin albumin nanoparticles to build targeting hypericin albumin nanoparticles, thus making hypericin albumin nanoparticles precisely reach corresponding lesion location to inhibit and kill *Escherichia coli*, so as to reach best therapeutic effect and minimize usage amount of drugs. Results showed that the concentration ratio of 1600:4:18:10 for hypericin albumin nanoparticle (mg):rabbit antiserum (μg):ethanediol (g) obtained the maximum mass of precipitates.

The present invention formed polyethylene glycol through irradiating ethanediol with carbon ion, which could precipitate and separate *Escherichia coli* serum antibody and hypericin albumin nanoparticle complex from solution, thus greatly reducing dissociative ethanediol molecules and dissociative hypericin albumin nanoparticle molecules. Coupling between antibody protein and hypericin albumin nanoparticles and ethanediol was not only simple mixing, but forming a relatively stable structure through irradiation cross-linking.

The present invention compared the results of polyacrylamide gel (PAGE) electrophoresis of combination complex of antibody protein and hypericin albumin nanoparticle with the results of polyacrylamide (PAGE) electrophoresis of mixture of antibody protein, hypericin albumin nanoparticles and PEG. The results of polyacrylamide gel (PAGE) electrophoresis of targeting complex showed a new electrophoretic band, which proved that antibody protein was combined with hypericin albumin nanoparticles and ethanediol in a certain way, changing molecular weight of the protein.

Embodiment 6

In vitro antimicrobial test of complex of *Escherichia coli* serum antibody, ethanediol and hypericin albumin nanoparticles:

Hypericin is a common antiviral substance in *Hypericum*, and belongs to dianthrone. Studies of phytochemistry and pharmacology showed that hypericin had characteristics of anti-depression, anti-tumor, anti-virus, hemostasis, anti-inflammatory and photoactive activity. At present, most studies on hypericin in China are in the stage of clinical pharmacological research, mainly focusing on adjuvant therapy for tumor and anti-virus research, while it has been used in clinic treatment for depressive disorder and AIDS in foreign countries. Hypericin has been used in studies in animal husbandry: it could be used in preventing and curing simple infection or mixed infection of diseases, such as high swine fever, porcine reproduction and respiratory syndrome, pseudorabies, swine fever, transmissible gastroenteritis and porcine parvovirus infection; it has extremely high killing effects for highly pathogenic H5N1 and H9N2 subtype avian influenza viruses. New preparation of hypericin developed by Lanzhou Institute of Husbandry and Pharmaceutical Sciences of CAAS has a final killing ratio for highly pathogenic avian influenza virus up to one hundred percent, through verification by authority organization. Therefore, hypericin and its new preparation has always been a hot spot of studies at home and abroad, as well as source of seeking bioactive components with development and application prospect. The research on bacteriostasis of hypericin albumin nanoparticle-*Escherichia coli* serum antibody complex has not been reported. To explore the bacteriostasis of hypericin albumin nanoparticle-*Escherichia coli* serum antibody complex, hypericin has been used to conduct in vitro studies on the antibacterial effects of hypericin on *staphylococcus aureus* and *Escherichia coli*, which is of great importance in further exploring pharmacologic action of hypericin.

Hypericin albumin nanoparticle-*Escherichia coli* serum antibody complex is planned to be used to detect the lowest minimal inhibitory concentration (MIC) to *Escherichia coli* and *Staphylococcus aureus* and determine the comparison of new preparation of this drug and original drug in antibacterial effect.

1. Materials and Methods:

1.1 Test Materials Standard Strains:

Strain: *Escherichia coli* (*E. coli*) $C_{4403}$ and *Staphylococcus aureus* (*S. aureus*) $C_{26112}$ are both purchased from Gansu Institute of Microbiology.

Reagents: pyridine, sodium chloride and sodium hydroxide were all analytically pure, hypericin (Shanghai Biochempartner Co., Ltd., content of 98%), targeting hypericin (self-manufactured). Peptone, agar powder and beef extract were common biochemical reagents.

1.2 Test Method for the First Group:

1.2.1 Preparation of Medium:

(1) Preparation of Solid Medium:

5 g of peptone, 5 g of sodium chloride, 2.5 g of yeast powder, 7.5 g-10 g of agar, 500 ml of distilled water, pH: 7.2-7.4 and sterilization at 121° C. for 20 min.

(2) Preparation of Liquid Medium:

5 g of peptone, 5 g of sodium chloride, 2.5 g of yeast powder, 500 ml of distilled water, pH: 7.2-7.4 and sterilization at 121° C. for 20 min.

1.2.2 Preparation of Bacterial Liquid:

An inoculating loop was used to pick up a small amount of refrigerated *Staphylococcus aureus* and *Escherichia coli* bacterial colonies respectively, suspended in classical liquid medium, revived at 37° C. for 24 hours, then conducted streak inoculation on classical liquid medium, cultivated at 37° C. until bacteria reached growth balance period, selected typical bacterial colony generation 2 to generation 3. After activity recovery, typical bacterial colonies were selected to inoculate on agar plate medium, typical bacterial colonies were taken to inoculate in liquid medium, and cultivates at 37° C. for 18 hours.

1.2.3 Preparation of Test Liquid:

The drugs were weighted, 500 ml of sterile pyridine solution was calculated and weighed according to the content of targeting hypericin and hypericin to prepare liquid with concentration of hypericin of 51.2 μm/ml.

1.2.4 Determination of the Minimal Inhibitory Concentration of Targeting Hypericin and Hypericin:

Double dilution method was applied to determine the minimal inhibitory concentration (MIC) of liquid to all tested bacteria. 10 sterile tubes were taken with tampon and numbered. 2.0 ml of sterile broth medium was added into each tube. Then 2.0 ml of prepared liquid containing hypericin of 51.2 μm/ml was added into the first tube, mixed evenly, and 2.0 ml was taken out to put in the second tube, and so on, to make double dilution until taking 2.0 ml from the eighth tube. The liquid concentrations of the eight tubes were 25.6 μg/ml, 12.8 μg/ml, 6.4 μg/ml, 3.2 μg/ml, 1.6 μg/ml, 0.8 μg/ml, 0.4 μg/ml and 0.2 μg/ml, respectively. In the ninth tube was added bacterial liquid instead of agentia as a positive control, while in the tenth tube was not added agentia or bacterial liquid as negative control. Three parallel samples were made for each tube, a sterile liquid medium was used to dilute the tested bacterial liquid for 100 times after cultivating in liquid medium for 18 hours. 0.1 ml of bacterial diluents were taken and added into the above Tube 1 to Tube 9 respectively. Tube 10 was added 0.1 ml of sterile normal saline. All tubes were set in constant temperature incubator for 24 hours and the results were observed. In positive control tubes, the growth of bacteria made the tubes appear muddy, while there was no bacterium grown in negative control tubes and the tubes appeared transparent. Under such preconditions, the muddy condition of other tubes was observed. If tubes appeared muddy, it indicated that bacteria grew in it; if tubes appeared transparent, it showed that no bacteria grew in it. Through eye observation, the tubes with no grown bacteria were selected, their liquid was taken and coated it on agar plate medium respectively, cultivated in constant temperature incubator for 24 hours, and results were observed. The agar plate with no grown bacteria and containing the lowest concentration of liquid was the minimal inhibitory concentration of the drug to the bacterial strain.

1.2.5 Preparation of a Nutrient Agar Medium:

The medium was prepared according to dosage in proportion: 2% of agar, 0.5% of beef extract, 1% of peptone, 0.5% of sodium chloride, which were weighed successively. The beef extract was picked by a glass rod and put into a small beaker or culture dish scrap of paper for weighing, and poured into a beaker after dissolving with hot water. Water of less than required amount was added into a beaker, heated, the components were added one by one, dissolved, the agar was added after boiling the solution, and continuously stirred during the process of melting. After being dissolved, required amount of water was complemented. The pH was adjusted to 7.4-7.6 with 4% NaOH. According to test requirements, the prepared medium was split and put it into a culture dish, bound with kraft paper after condensation, sterilized with 121° C. high temperature circulating steam for 15 minutes.

1.3 Test Method for the Second Group: 1.3.1 Preparation of a medium:

(1) Preparation of Solid Medium:

5 g of peptone, 5 g of sodium chloride, 2.5 g of yeast powder, 7.5 g-10 g of agar, 500 ml of distilled water, pH: 7.2-7.4 and sterilization at 121° C. for 20 min.

(2) Preparation of Liquid Medium:

5 g of peptone, 5 g of sodium chloride, 2.5 g of yeast powder, 500 ml of distilled water, pH: 7.2-7.4 and sterilization at 121° C. for 20 min.

1.3.2 Preparation of a Bacterial Liquid:

An inoculating loop was used to pick up a small amount of refrigerated *Staphylococcus aureus* and *Escherichia coli* bacterial colonies respectively, suspended in classical liquid medium, revived at 37° C. for 24 hours, then streak inoculation on classical liquid medium, cultivated at 37° C. until bacteria reach growth balance period, selected typical bacterial colony generation 2 to generation 3. After activity recovery, typical bacterial colonies were selected to inoculate on agar plate medium, cultivated at 37° C. for 28 hours, typical bacterial colonies were taken to inoculate in liquid medium, and cultivated at 37° C. for 18 hours.

1.3.3 Determination of the Minimal Inhibitory Concentration of Targeting Hypericin and Hypericin:

Double dilution method was used to determine the minimal inhibitory concentration (MIC) of liquid to all tested bacteria. 10 sterile tubes were taken with tampon and numbered. 2.0 ml of sterile broth medium was added into each tube. 20 culture dishes inoculated with *Escherichia coli* and *Staphylococcus aureus* respectively were divided into two groups, 10 culture dishes for each group. Two groups of culture dish inoculated with *Staphylococcus aureus* were respectively added into tubes of hypericin liquid and tubes of targeted hypericin liquid with concentration of 6.4 µg/ml, 12.8 µg/ml and 25.6 µm/ml prepared with pyridine as solvent. Two groups of culture dish inoculated with *Escherichia coli* were respectively added into tubes of hypericin liquid and tubes of targeting hypericin liquid with concentration of 3.2 µg/ml, 6.4 µg/ml and 12.8 µg/ml prepared with pyridine as solvent and tubes. Cultivated in a constant temperature incubator at 37° C. for 24 hours.

2. Results 2.1 Measured Results of the Minimal Inhibitory Concentration of Hypericin Liquid and Targeting Hypericin Liquid:

2.1.1 Minimal Inhibitory Concentration of Hypericin Liquid and Targeting Hypericin Liquid for Two Kinds of Bacteria:

See Table 3 for the minimal inhibitory concentration of hypericin liquid and targeting hypericin liquid to *Escherichia coli*.

TABLE 3

| Group | Number | | | | | | | | | |
|---|---|---|---|---|---|---|---|---|---|---|
|  | 1 | 2 | 3 | 4 | 5 | 6 | 7 | 8 | 9 | 10 |
| Group I | − | − | − | − | ± | + | + | + | + | − |
| Group II | − | − | − | − | − | − | − | + | + | − |

See Table 4 for the minimal inhibitory concentration of hypericin liquid and targeting hypericin liquid to *staphylococcus aureus*.

TABLE 4

| Group | Number | | | | | | | | | |
|---|---|---|---|---|---|---|---|---|---|---|
|  | 1 | 2 | 3 | 4 | 5 | 6 | 7 | 8 | 9 | 10 |
| Group I | − | − | − | − | ± | + | + | + | + | − |
| Group II | − | − | − | − | − | − | + | + | + | − |

Clear tubes were selected, their liquid was take out and was coated on the agar plate medium respectively, cultivated in the constant temperature incubator for 24 hours, the number of tubes with no bacteria grown on plate was recorded, and the minimal inhibitory concentration was obtained.

See the Table 5 for the minimal inhibitory concentration of targeting hypericin and hypericin to two kinds of bacteria.

TABLE 5

| Test bacteria | contrast test (µg/ml) | |
|---|---|---|
|  | 1 | 2 |
| *Escherichia coli* | 0.4 | 6.4 |
| *Staphylococcus aureus* | 0.8 | 6.4 |

The data of the above table showed that the minimal inhibitory concentration of hypericin for *Escherichia coli* was 0.4 µg/ml, while the minimal inhibitory concentration of hypericin for *staphylococcus aureus* was 0.8 µg/ml. The sensitivity of *Escherichia coli* was higher than that of *staphylococcus aureus*.

3. Discussion

As a common active material in *Hypericum*, hypericin belongs to dianthrone and is widely distributed. According to studies of modern phytochemistry and pharmacology, hypericin has obvious effects on anti-depression, AIDS treatment, hemostasis and anti-inflammatory and so on. It is widely used in the clinic. In recent years, although a great deal of work has been done in pharmacological studies and certain results have been obtained, studies on the bacteriostatic action to Gram negative and positive bacteria have not been reported. Therefore, the present invention takes *Escherichia coli* and *Staphylococcus aureus* as research objects, test the minimal inhibitory concentration of targeting hypericin and hypericin on the two kinds of bacteria, and compare bacteriostasis in different drug concentrations. It has great significance in understanding that whether the target hypericin and hypericin have bacteriostasis and how about the antibacterial effect thereof, and determining the dosage of hypericin and researching on the antibacterial mechanism. Tests showed that the sensitivity of hypericin was lower than that of targeting hypericin both for *Escherichia coli* and *Staphylococcus aureus*. The sensitivity of hypericin to *Escherichia coli* was roughly consistent with that of targeting hypericin to *Escherichia coli*, but sensitivity of hypericin to *Staphylococcus aureus* was slightly lower than that of targeting hypericin to *Staphylococcus aureus*.

Embodiment 7

Pharmacodynamic verification for *Escherichia coli* serum antibody, ethanediol and hypericin albumin nanoparticle complex:

As a common poultry disease and frequently-occurring disease, colibacillosis has serious hazard for poultry industry. This disease has become increasingly serious in various countries, causing huge economic losses. Chicken colibacillosis is a common bacterial infectious disease caused by some serotypes of *Escherichia coli* (*E. coli*), including *E. coli* granuloma, peritonitis, salpingitis, omphalitis, synovitis, air sacculitis, ophthalmitis and vitelline peritonitis. Chicken colibacillosis mainly happens in chick phase and egg-laying phase of adult laying hens and has serious hazard for peak laying hens especially. This infectious disease has a morbidity of 11%-69%; mortality rate of 3.8%-72.9%; and fatality rate of 40.2%-90.3%. In recent years, several outbursts of chicken colibacillosis have brought serious economic losses to poultry industry in the world. Chicken colibacillosis has attracted more and more attention from governments, researchers and poultry farmers of various countries. Poultry enterprises or famers in most areas in China still apply antibacterial agents to implement prevention and treatment. Long-term antibacterial agent abuse makes chicken *E. coli* epidemic strain generate wide range of resistance to many kinds of antibacterial agents. Long-term use of effective antibiotics will eventually generate drug-resistant strains. Antibacterial agents have poor prevention and treatment effects, increasing drug-resistant strains and continuously widened drug-resistant spectrum. Meanwhile, residual of antibiotic medicine becomes prominent.

1. Materials and Methods:
1.1 Materials
1.1.1 Hypericin (Shanghai Biochempartner Co., Ltd. content of 98%), targeting hypericin (self-manufactured). The above two kinds of raw materials were taken to prepare preparations containing 10% of hypericin.
1.1.2 Standard Strain:
   *Escherichia coli* (*E. coli*) $C_{4403}$,
   *Pasteurella multocida* (*P. multocid*) $C_{44-1}$,
   *Staphylococcus aureus* (*S. aureus*) $C_{26112}$,
   all purchased from Gansu Institute of Microbiology.
1.1.3 Experimental animals:
   One hundred of healthy Kunming-mice, half and half for male and female, with the body weight of 18-22 g, were all purchased from Experimental Animal Department of Lanzhou University. The laboratory controlled room temperature at 18-22° C. and relative humidity at 40-70%, and kept indoor ventilation. Male and female mice were kept and fed in different cages. Padding at the bottom of cages was sawdust after sun exposure. Every other day, the cages were cleaned, the padding was replaced and the cages were sterilized. Feed was full nutritional solid particles rat feed provided by small animal laboratory of Lanzhou Institute of Husbandry and Pharmaceutical Sciences of CAAS, containing about 21% of protein. Mice could intake food and drink water freely.
1.1.4 Sick poultry:
   Sick chicken were from a chicken farm in Lintao, Gansu. Sick chicken were 45-day-old meat chicken with symptoms of diarrhea, fluffy feathers, lassitude, poor appetite and higher mortality rate. Variation of anatomy: cloudy peritoneum, a large amount of exudation in body cavity, viscera adhesion.
1.1.5 *Escherichia coli* serum antibody-hypericin albumin nanoparticle complex (targeting complex): self-manufactured, transparent solution containing 10 g/mL of hypericin, standby application.
1.1.6 *Escherichia coli* serum antibody: self-manufactured, indirect ELISA titer was 1:1024.
1.1.7 Fluorescent antibody: purchased from Beijing Dingguo Biotechnology Development Center, batch number Y2300141.
1.1.8 Medium and solution:
   (1) Materials for bacteriostasis in vitro and microbiology diagnostic tests:
   Nutrient broth, common agar medium, MacConkey agar, sugar fermentation medium, triple sugar iron agar (TSI) and VP reagent (liquid A: α-naphthol alcohol solution (5 g of α-naphthol and 100 mL of absolute alcohol), liquid B: KOH solution (40 g of KOH and 100 mL of water). Liquid A and liquid B were put into brown bottles respectively and store at 4-10° C. and prepared according to conventional method.
   (2) Preparation of mofalande turbidimeter: preparing standard barium sulfate suspension and implementing turbidity determination.
   (3) Indirect immunofluorescent compound: pH7.4, 0.1M phosphate buffer.
1.2 Method:
1.2.1 Targeting Complex Cures Chicken Colibacillosis:
   Rapid Diagnosis by Immunofluorescence Technique:
   Under sterility condition, the faeces of chicken with symptoms and lesion of colibacillosis or intestinal content of dead chicken were taken, sterilized normal saline was added to dilute it by 1:5, still standing, used as a pathological sample. The treated pathological sample was inoculated to mice through enterocoelia, 0.5 ml for each mouse. Mice were fed in temporary-keeping room, sufficient water and feed were provided, and mice were observed. After the death of mice, mice were dissected, their livers were taken and grounded, and were diluted with normal saline according to the proportion of 1:5. After still standing for 5 minutes, supernatant liquid was taken, timing was started after fully mixing the supernatant liquid with the targeting complex in a ratio of supernatant liquid:serum antibody=4:1. Coating started at 10 min, inoculating loop was used to pick the mixed liquor. After drying up, the mixed liquor was fixed with acetone, fluorescent antibody was added for dilution and dyeing. It was observed under fluorescence microscope after drying up.

Targeting Complex Cured Chicken Colibacillosis:

Grouping of experimental chickens: the sick chickens were divided into 4 groups, 50 chickens for each group, and mark them. Different drugs for treatment were applied.

An intramuscular injection was applied, No drug was added in feed and drinking water. Drug administration and administration method for each treatment group:

See Table 6 for drug administration and administration method for each treatment group.

TABLE 6

| Group | Medication method | Dose (mg/Kg) | Frequency of drug administration (times/d) | Course of treatment (d) |
|---|---|---|---|---|
| Hypericin | Intramuscular injection | 2.00 | 2 | 1 |
| Targeting high dose conjugate | Intramuscular injection | 2.00 | 1 | 1 |
| Targeting middle dose conjugate | Intramuscular injection | 1.00 | 1 | 1 |
| Targeting law dose conjugate | Intramuscular injection | 0.50 | 1 | 1 |

Symptom observation after drug administration: the clinical changes and death of chicken in all groups were carefully observed and recorded.

Evaluation Standard:

Cure: chickens stopped dying after a course of treatment, with normal energy and appetite.

Effective: after a course of treatment, chickens stopped dying, energy was improved and appetite was increased.

Invalid: after a course of treatment, main symptoms had no improvement or disease developed.

2. Results and Analysis:

2.1 Treatment of Complex *Escherichia coli* Animal Model:

Treatment effects of colibacillosis animal model showed that, compared with hypericin in control group, by applying targeting high concentration hypericin complex to inject 1.0 mL/mouse by intramuscular injection, the effective rate and cure rate after one time of drug administration were 100% and 90% respectively; by applying targeting middle concentration hypericin complex to inject 1.0 mL/mouse by intramuscular injection, the effective rate and cure rate after one time of drug administration were 100% and 75% respectively; by applying targeting low concentration hypericin complex to inject 1 mL/mouse by intramuscular injection, the effective rate and cure rate after one time of drug administration were 100% and 65%, respectively. While in hypericin control group, by applying hypericin injection to inject 1.0 mL/mouse by intramuscular injection, the effective rate of pathogenetic mice was 90% and the cure rate was 33.3%. *Escherichia coli* serum (antibody) control group was invalid in treatment. See Table 7 for curative effects of original drug and targeting drug mice colibacillosis, namely curative effects of colibacillosis animal model.

TABLE 7

| Group and total cured amount | Effective | Cure | Effective rate % | Cure rate % |
|---|---|---|---|---|
| Rabbit antiserum | 30 | 0 | 0 | 0 |
| Hypericin | 30 | 27 | 10 | 90 | 33.3 |
| Targeting high concentration hypericin complex | 30 | 30 | 27 | 100 | 90 |
| Targeting middle concentration hypericin complex | 30 | 30 | 22 | 100 | 75 |
| Targeting low concentration hypericin complex | 30 | 30 | 18 | 100 | 65 |

2.2 Complex Treats Chicken Colibacillosis:

Indirect immunofluorescence rapid diagnosis: through indirect immunofluorescence rapid diagnosis, it could be determined that pathogeny of this disease was pathogenic *Escherichia coli*. Combining with clinical symptom observation and autopsy observation, this disease could be diagnosed as chicken colibacillosis.

All groups of drugs in treating chicken colibacillosis: targeting complex was given for 1st day to all dose groups, symptoms of chickens were obviously relieved and targeting high dose group stopped dying on 2nd day and appetite and energy of chickens recovered basically. The therapeutic effects of targeting middle dose group remained the same as that of high dose group; chickens in targeting low dose group stopped dying on 2nd day, symptom of diarrhea disappeared basically, and appetite and energy of chickens were recovered basically on 3 rd day. Symptoms in hypericin group begin to relieve on 2nd day after drug administration, symptom of diarrhea basically disappeared on 4th day, and appetite and energy of chickens were recovered on 5th day. The above data showed that the high, middle and low doses of targeting complex conjugate injection had significant curative effects on chicken colibacillosis, with effective rate and cure rate of 100%, 100% and 92% respectively; while the effective rate and cure rate of hypericin group was 80% respectively. Seeing from changes of symptoms, compared with hypericin group, all dose groups of targeting hypericin conjugate had a faster speed in improving diarrhea symptom and recovering mental state of chickens after drug administration, and it improved diarrhea symptom and recovering mental state of chickens more quickly. See Table 8 for results of curative effects of original drug and targeting drug on chicken colibacillosis.

TABLE 8

| Group | Total amount of treated ones | Total amount of effective ones | Total amount of cured ones | Effective rate (%) | Cure rate (%) |
|---|---|---|---|---|---|
| Hypericin | 50 | 40 | 35 | 80 | 70 |
| High dose conjugate | 50 | 50 | 50 | 100 | 100 |
| Middle dose conjugate | 40 | 50 | 50 | 100 | 100 |
| Low dose conjugate | 50 | 46 | 45 | 92 | 90 |

2.3 Analysis:

Therapeutic outcomes of complex to chicken colibacillosis showed that the symptoms of sick chickens in all dose groups of targeting complex were relieved obviously on 1st day of drug administration. Chickens in targeting high dose group stopped dying on 2nd day and the appetite and energy of chickens recovered basically. The therapeutic effects of targeting middle dose group remained the same as that of high dose group; chickens in targeting low dose group stopped dying on 2nd day, symptom of diarrhea disappeared basically, and appetite and energy of chickens were recovered basically on 3 rd day. Symptoms in hypericin group begin to relieve on 2nd day after drug administration, symptom of diarrhea basically disappeared on 4th day, and appetite and energy of chickens were recovered on 5th day. The above data showed that the high, middle and low doses of targeting complex injection had significant curative effects on chicken colibacillosis. Seeing from changes of symptoms, compared with hypericin group, all dose groups of targeting hypericin conjugate had a faster speed in improving diarrhea symptom and recovering mental state of chickens after drug administration, and it improved diarrhea symptom and recovering mental state of chickens more quickly. After rapid diagnosis by immunofluorescence technique, mouse serum antibody and targeting complex were taken and fully mixed, then timing started, dying was conducted, the mixture was observed under fluorescence microscope after drying up. The following conclusions were drawn: *Escherichia coli* serum antibody is antiserum and can combine with various types of *Escherichia coli*. Therefore, targeting of a complex is specificity of *Escherichia coli*, but it can treat colibacillosis of various animals.

Finally, it shall be described that the above mentioned only provides preferred embodiments of the present invention, instead of being used to restrict the present invention. Although the present invention has been described in details with reference to the above embodiments, those skilled in the art can also modify the technical solutions recorded in above embodiments or implement equivalent replacement for some technical characteristics. Any modification, equivalent replacement and improvement within the spirit and principles of the present invention shall be included in the scope of the present invention.

The invention claimed is:

1. A hypericin albumin nanoparticle-*Escherichia coli* serum antibody complex is characterized by being prepared through the following steps:
   1) mixing hypericin albumin nanoparticles and rabbit anti-*Escherichia coli* to obtain a mixed liquor;
   2) adding the mixed liquor from Step 1) into ethanediol to obtain a ethanediol mixed liquor;
   3) irradiating the ethanediol mixed liquor from Step 2) with carbon ion, placing the mixed liquor at −2° C.-5° C. for 2 hours after irradiation to obtain an irradiated ethanediol mixed liquor;
   4) centrifuging the irradiated ethanediol mixed liquor from Step 3) at a low temperature, discarding a supernatant, and freezing and drying precipitates to obtain the hypericin albumin nanoparticle-*Escherichia coli* serum antibody complex,
   wherein the hypericin albumin nanoparticles and the rabbit anti-*Escherichia coli* are mixed according to the ratio of (800-1600) mg:(4-10) μg in Step 1);
   wherein the ratio of hypericin albumin nanoparticles: ethanediol is (800-1600) mg (12-30) g in Step 2);
   wherein the irradiation dose of carbon ion is 3-10 Gy in Step 3); and
   wherein the temperature of the low temperature centrifugation is −2° C.-5° C., the centrifugal rotational speed is 16500 r/min and the cryogenic temperature of precipitates is −2-0° C. in Step 4).

2. The hypericin albumin nanoparticle-*Escherichia coli* serum antibody complex according to claim 1, characterized in that the hypericin albumin nanoparticles and rabbit anti-*Escherichia coli* are mixed according to the ratio of 1600 mg:4 μg in Step 1); the ratio of hypericin albumin nanoparticle:ethanediol is 1600 mg:12 g in Step 2); the irradiation dose of carbon ion is 5 Gy and the setting temperature is 0° C. in Step 3); the temperature of low temperature centrifugation is 0° C., the centrifugal rotational speed is 16500 r/min and the cryogenic temperature of precipitates is −1° C. in Step 4).

3. A preparation method for hypericin albumin nanoparticle-*Escherichia coli* serum antibody complex is characterized by the following steps:
   1) mixing hypericin albumin nanoparticles and rabbit anti-*Escherichia coli* to obtain a mixed liquor;
   2) adding the mixed liquor from Step 1) into ethanediol to obtain an ethanediol mixed liquor;
   3) irradiating the ethanediol mixed liquor from Step 2) with carbon ion, placing the ethanediol mixed liquor at −2° C.-5° C. for 2 hours after irradiation to obtain an irradiated ethanediol mixed liquor;
   4) centrifuging the irradiated ethanediol mixed liquor from Step 3) at a low temperature, discarding a supernatant, and freezing and drying precipitates to obtain the hypericin albumin nanoparticle-*Escherichia coli* serum antibody complex;
   characterized in that the hypericin albumin nanoparticles and rabbit anti-*Escherichia coli* are mixed according to the ratio of (800-1600)mg:(4-10)μg in Step 1); the ratio of hypericin albumin nanoparticle:ethanediol is (800-1600)mg:(12-30)g in Step 2); the irradiation dose of carbon ion is 3-10 Gy in Step 3); the temperature of low temperature centrifugation is −2° C.-5° C., the centrifugal rotational speed is 16500 r/min and the cryogenic temperature of the precipitates is −2-0° C. in Step 4).

4. The preparation method for hypericin albumin nanoparticle-*Escherichia coli* serum antibody complex according to claim 3, characterized in that the hypericin albumin nanoparticles and rabbit anti-*Escherichia coli* are mixed according to the ratio of 1600 mg:4 μg in Step 1); the ratio of hypericin albumin nanoparticle:ethanediol is 1600 mg:12 g in Step 2); the irradiation dose of carbon ion is 5 Gy and temperature for placing the ethanediol mixed liquor for 2 hours after irradiation is 0° C. in Step 3); the temperature of low temperature centrifugation is 0° C., the centrifugal rotational speed is 16500 r/min and the cryogenic temperature of the precipitates is −1° C. in Step 4).

* * * * *